United States Patent [19]

Cooper

[11] Patent Number: 5,626,622
[45] Date of Patent: May 6, 1997

[54] DUAL SENSOR RATE RESPONSIVE PACEMAKER

[75] Inventor: Daniel Cooper, Lakewood, Colo.

[73] Assignee: Telectronics Pacing Systems, Inc., Englewood, Colo.

[21] Appl. No.: 309,760

[22] Filed: Sep. 21, 1994

[51] Int. Cl.⁶ ............................................. A61N 1/368
[52] U.S. Cl. ............................................. 607/18
[58] Field of Search ........................ 607/18, 19, 20, 607/17

[56] References Cited

U.S. PATENT DOCUMENTS

| | | | |
|---|---|---|---|
| 4,702,253 | 10/1987 | Nappholz et al. | 128/419 |
| 4,766,901 | 8/1988 | Callaghan | 128/419 |
| 4,782,836 | 11/1988 | Alt | 128/419 |
| 4,860,751 | 8/1989 | Callaghan | 128/419 |
| 4,901,725 | 2/1990 | Nappholz et al. | 128/419 |
| 4,905,697 | 3/1990 | Heggs et al. | 128/419 |
| 4,926,863 | 5/1990 | Alt | 128/419 |
| 4,945,909 | 8/1990 | Fearnot et al. | 607/18 |
| 5,101,824 | 4/1992 | Lekholm | 128/419 |
| 5,197,467 | 3/1993 | Steinhaus et al. | 128/419 |
| 5,201,808 | 4/1993 | Steinhaus et al. | 128/419 |
| 5,376,106 | 12/1994 | Stahmann et al. | 607/18 |

*Primary Examiner*—William E. Kamm
*Assistant Examiner*—Kennedy J. Schaetzle
*Attorney, Agent, or Firm*—Gottlieb, Rackman & Reisman

[57] ABSTRACT

An electronic pacemaker generating pacing signals includes both a metabolic rate responsive sensor monitoring a physiological parameter and an activity rate responsive sensor monitoring movement of a patient's body during exercise. The measurements from each of the sensors are used to develop a corresponding rate signal and the two signals are combined to generate a dual sensor rate used to determine the timing of the pacing signals. The physiological parameter may be for example minute volume variation while the body movement may be monitored for example by using an accelerometer. The activity rate responsive sensor output is preferably used as an indication of a transition of a level of exercise, when a faster change in the pacing rate is desirable.

29 Claims, 12 Drawing Sheets

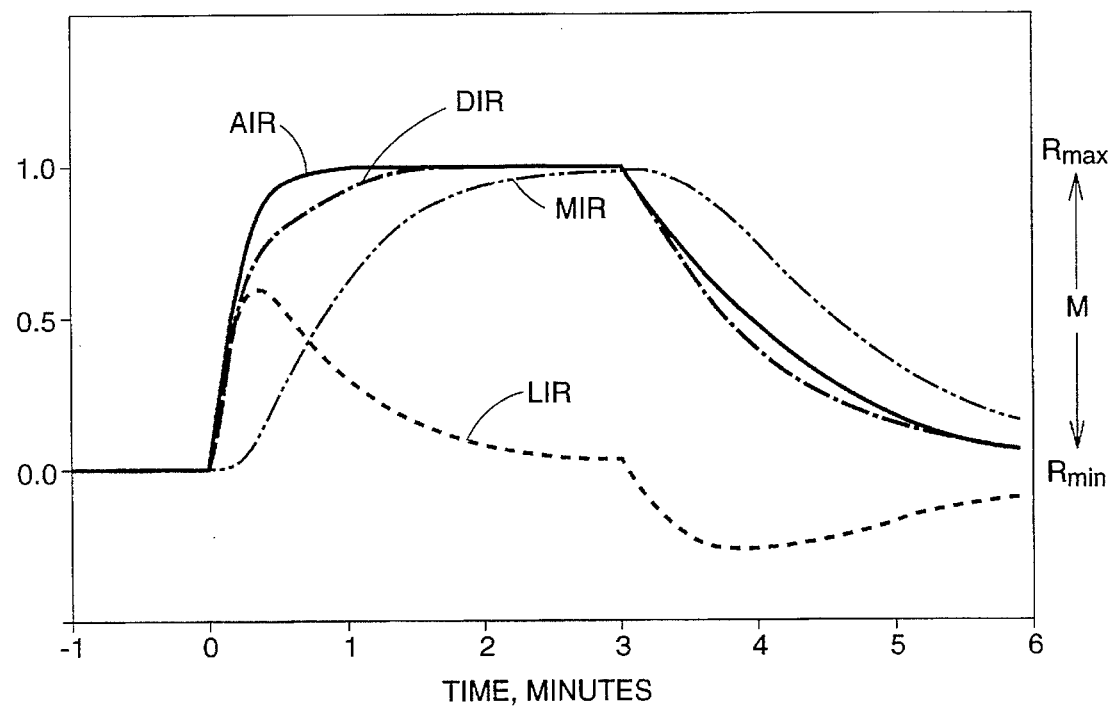
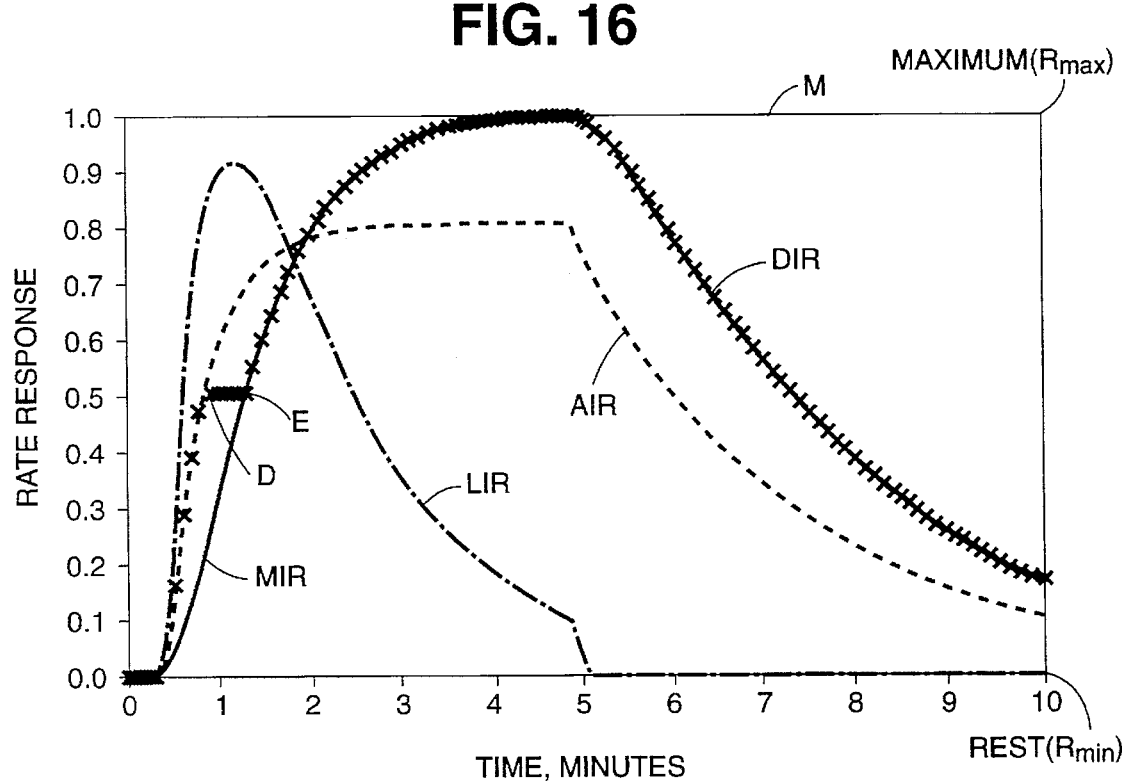

DUAL SENSOR RATE RESPONSIVE PACEMAKER

BACKGROUND OF THE INVENTION

1. Field of the Invention

This invention relates to rate responsive pacemakers and, more particularly, to rate responsive pacemakers that combine the outputs of both an activity sensor and a metabolic demand sensor in order to respond promptly, during exercise, to changes in a patient's metabolic demand.

2. Description of the Prior Art

Many attempts have been made to control the heart rate of a pacemaker patient so that it will duplicate the intrinsic heart rate of a healthy person both when the patient is at rest and when the patient is involved in various levels of exercise (i.e., so that the pacemaker will be truly rate responsive). Metabolic-related parameters heretofore proposed for controlling the pacing rate include the QT interval, respiration rate, venous oxygen saturation, stroke volume, venous blood temperature, and minute volume, among others. In addition, the use of mechanical and electrical sensors which detect patient motion have also been explored in attempts at achieving improved rate-responsiveness.

However, the metabolically-related parameters used for controlling rate responsive pacemakers tend to react slowly in reflecting changes in the patient's level of exercise. This can result in the patient having a hemodynamic deficiency due to the lag time involved between the onset of a new level of exercise and the reaction thereto by the pacemaker.

Mechanical/electrical motion sensors, on the other hand, respond quite rapidly to changes in the patient's level of exercise. However, they frequently provide an erroneous level of activity due to movement caused by other types of activities such as travel in a vehicle.

More recently, attempts have been made to develop dual-sensor rate responsive pacemakers in order to compensate for deficiencies found in earlier rate-responsive pacemakers making use of a single sensor. An example of such a dual-sensor rate-responsive pacemaker may be seen in U.S. Pat. No. 4,782,836 to E. Alt, entitled "Rate Adaptive Cardiac Pacemaker Responsive To Patient Activity And Temperature" and which issued on Nov. 8, 1988. This patent discloses the use of an activity (motion) sensor in conjunction with a temperature sensor. The patent employs two algorithms relating blood temperature to pacing rate, one for an inactive condition of the patient, and another for an active condition of the patient. The motion sensor selects one or the other of the algorithms depending on the activity level of the patient.

U.S. Pat. No. 4,860,751 to F. J. Callaghan, entitled "Activity Sensor For Pacemaker Control", and which issued Aug. 29, 1989, also relates to a dual-sensor rate-responsive pacemaker. In this patent, a cardiac pacer is provided with both an activity sensor and a physiological sensor. The output of the activity sensor is utilized by control circuitry to enable the physiological sensor to monitor a selected physiological parameter only if the physical activity of the patient exceeds a selected threshold. This allows the electrical energy requirements of the pacer to be reduced.

U.S. Pat. No. 4,905,697 to K. S. Heggs et al., entitled "Temperature-Controlled Cardiac Pacemaker Responsive To Body Motion", and which issued Mar. 6, 1990, discloses the use of a motion sensor to cause the pacing rate to decrease upon cessation of exercise, after there has been an increase in the pacing rate, based on sensed blood temperature changes.

U.S. Pat. No. 4,926,863 to E. Alt, entitled "Rate Responsive Cardiac Pacemaker", and which issued May 22, 1990, discloses a dual-sensor rate-responsive pacemaker that employs activity sensing and temperature sensing. An accelerometer is used to sense physical activity of the patient. The activity sensor converts mechanical movement of the patient to a corresponding electrical signal, and only a portion of the electrical signal, in a frequency range below 4 Hz, is used to discriminate against signal components (e.g., environmental noise) arising from other than the patient's physical activity. This signal is combined with a sensed physiological parameter signal to confirm the metabolic state of the patient.

U.S. Pat. No. 5,101,824 to A. Lekholm, entitled "Rate-Responsive Pacemaker With Circuitry For Processing Multiple Sensor Inputs", and which issued Apr. 7, 1992, discloses a rate-responsive pacemaker employing two or more sensors that are indicative of metabolic demand to realize the advantages of both sensors in a circuit producing a rate command signal. This signal is used to operate the pacer at an optimum pacing rate to match the patient's physiological need. An addressable rate matrix, which is used to produce a specific rate unique to each combination of sensor inputs measured at a particular time, is employed in this patent. The sensor inputs include activity as well as a number of other physiological parameters.

U.S. Pat. No. 5,197,467 to B. M. Steinhaus et al., entitled, "Multiple Parameter Rate-Responsive Cardiac Stimulation Apparatus", and which issued Mar. 30, 1993, discloses a rate responsive pacemaker which uses a single impedance measuring circuit to sense multiple parameters for rate adaptation. The impedance-measuring circuit employs a measuring current having frequency components which may be varied in order to control the selection of the physiological parameters that are to be sensed, and the apparatus analyzes the physiological parameters and determines the best pacing rate to be selected based on such analysis.

OBJECTIVES AND SUMMARY OF THE INVENTION

An objective of the present invention is to provide a dual rate response sensor for a pacemaker which takes advantage of the information developed from two different types of detectors to develop a fast rate response.

A further objective is to provide a rate response sensor for a pacemaker with built in safeguards to insure that the pacemaker operates safely and reliably at all times.

Yet another objective is to provide an improved pacemaker which can provide rate responsive pacing accurately for a patient involved in various levels and durations of physical activities.

Other objectives and advantages of the invention shall become apparent from the following description. Typically a patient's physical activity such as exercise can be partitioned into five periods: an initial relaxed, or rest period with a low rest level of physical activity; exercise onset period, during which the patient's activity increases from the initial level toward a peak level; steady exercise period, during which the physical activity takes place generally at a steady level higher than the rest level; exercise termination period; during which the level of physical activity declines steadily toward the rest level; and a final rest period similar to the initial rest period.

A pacemaker constructed in accordance with this invention provides a rate responsive sensor receiving inputs from two different types of sensors: an activity sensor which generates an activity indicated rate response related to the instantaneous physical activity of the patient, and a metabolic sensor which generates a metabolic indicated rate response related to the corresponding metabolic demand of the patient. Intrinsically, the response of the activity sensor is very fast. On the other hand, the response of the metabolic demand sensor is normally relatively slow.

While the metabolic demand sensor provides a rate response which reflects accurately the intrinsic response during the steady state periods, i.e., the initial and final rest periods and the steady exercise period, because of its slow response, it is not ideally suited for the second and fourth periods during which the physical activity level undergoes a transition.

For this reason, the responses of the two sensors are combined in such a manner that when the physical activity undergoes a transition, the combined response is predominantly derived from the physical activity sensor. However, during steady state periods, i.e., rest, or constant physical activity periods, the combined response is predominantly derived from the metabolic rate sensor. Preferably a transition in the physical activity is determined by monitoring the output of the physical activity sensor. This can be accomplished, for example, by using a high pass filter on the output of the physical activity sensor.

Preferably the activity sensor uses an accelerometer to monitor the actual, physical movements of the patient. A plurality of acceleration signals exceeding a preselected range are indicative of increased physical activity of the patient and are used to derive the activity indicated response rate.

The metabolic demand sensor preferably includes an impedance measurement means for measuring a characteristic impedance of the body. The measurement thus obtained is used to derive the metabolic indicated response rate.

BRIEF DESCRIPTION OF THE FIGURES

FIG. 13 shows details of the cross-check circuit for the embodiment of FIG. 10;

FIGS. 16–19 show the dual indicated rate signal developed by the embodiment of FIG. 15 for various types of exercises.

DETAILED DESCRIPTION OF THE INVENTION

FIGS. 1–4 show details of a pacemaker 10 for sensing and pacing a heart 11. Except as noted, the operation of this pacemaker is described in detail in commonly assigned copending application Ser. No. 226,654 filed on Apr. 12, 1994 by T. Nappholz entitled FORCED ATRIOVENTRICULAR SYNCHRONY DUAL CHAMBER PACER, incorporated herein by reference, together with the patents cited therein.

Figure 1:
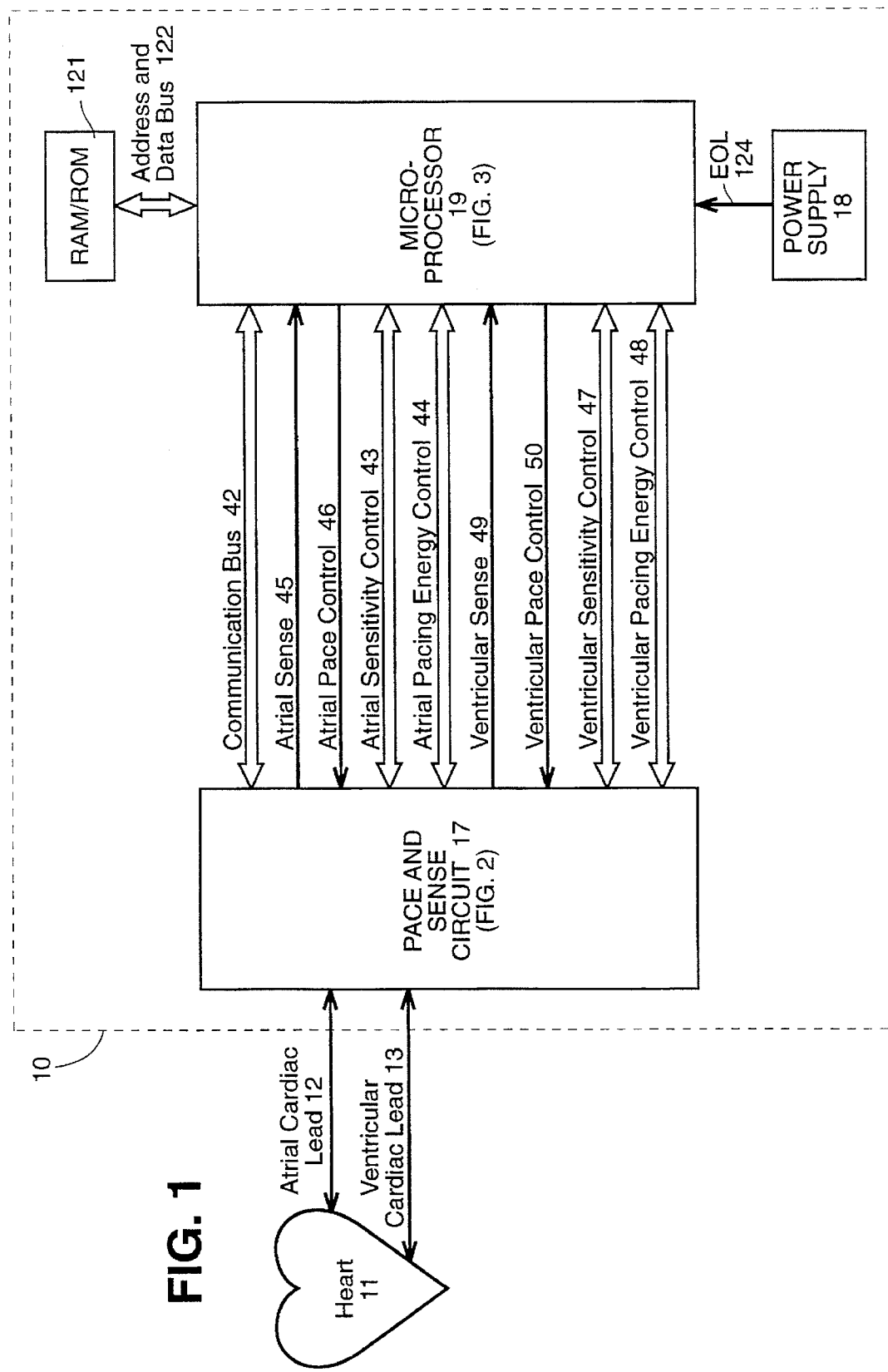
FIG. 1 shows a block diagram of a pacemaker constructed in accordance with this invention.

Briefly, FIG. 1 shows a block diagram of a pacemaker 10. The pacemaker 10 is designed to be implanted in a patient and is connected to appropriate leads for electrically coupling the pacemaker to the patient's heart 11. More specifically, an atrial cardiac lead 12 is used which extends to the atrium for the administration of pacing therapy to the atrium, and a ventricular cardiac lead 13 is used which extends to the ventricle of the patient's heart for the administration of pacing therapy to the ventricle. The pacemaker 10 includes a pace and sense circuit 17 for the detection of analog signals representing cardiac electrical activity and for the delivery of pacing pulses to the heart; a microprocessor 19 which, in response to numerous inputs received from the pace and sense circuit 17, performs operations to generate different control and data outputs to the pace and sense circuit 17; and a power supply 18 which provides power to the pace and sense circuit 17 and the microprocessor 19 by electrical conductors (not shown).

The microprocessor 19 is connected to a random access memory/read only memory unit 121 by an address and data bus 122. An end-of-life signal line 124 is used to provide, to the microprocessor 19, a logic signal indicative of a low power level of the power supply 18. The microprocessor 19 and the pace and sense circuit 17 are interconnected by a plurality of data and control means including a communication bus 42, an atrial sense line 45, an atrial pacing control line 46, an atrial sensitivity control bus 43, an atrial pace energy control bus 44, a ventricular sense line 49, a ventricular pace control line 50, a ventricular sensitivity control bus 47, and a ventricular pacing energy control bus 48.

Figure 2:
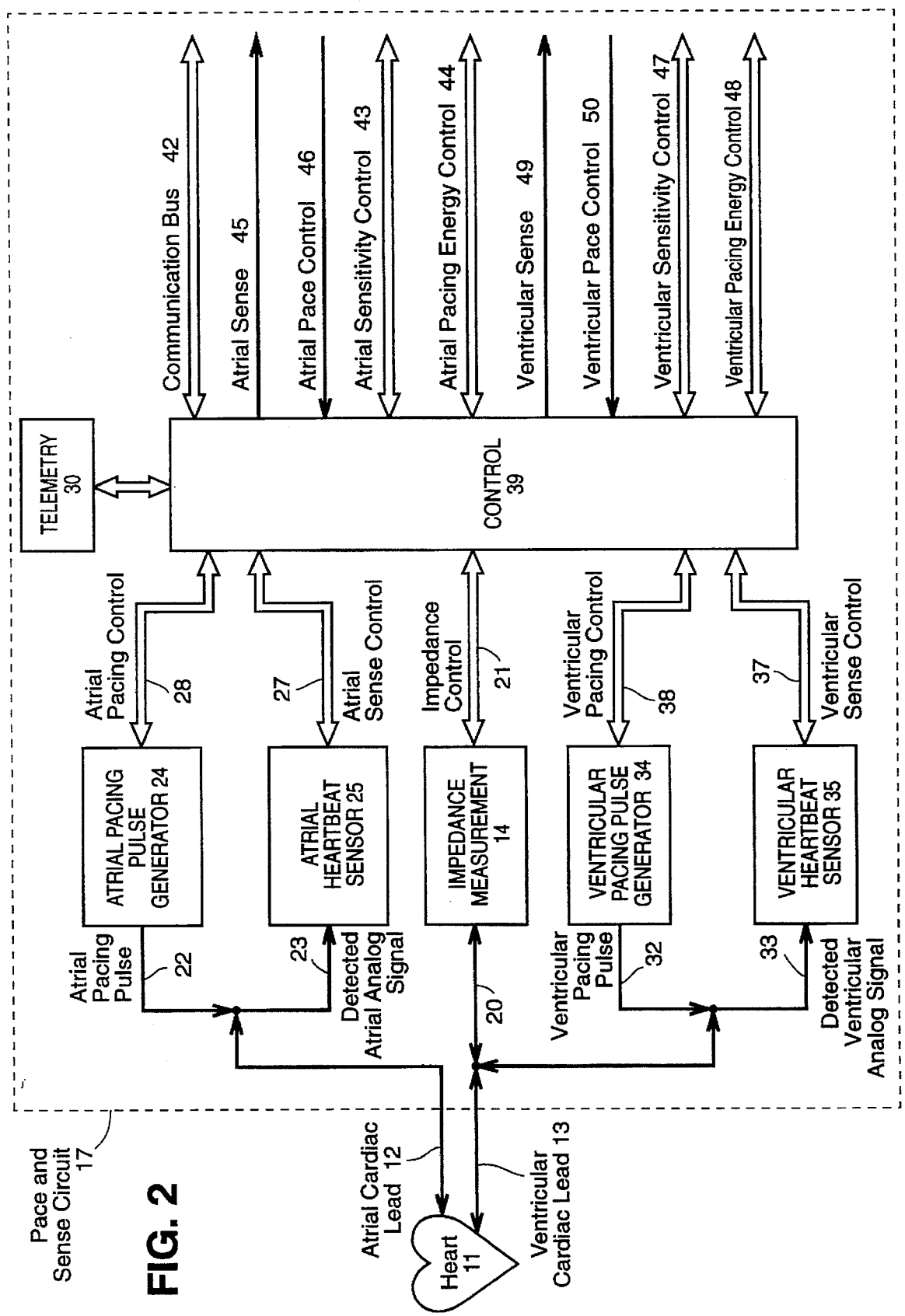
FIG. 2 shows details of the pace and sense circuit for the pacemaker of FIG. 1.

FIG. 2 shows the pace and sense circuit 17 which includes circuitry for an atrial pacing pulse generator 24, a ventricular pacing pulse generator 34, an atrial heartbeat sensor 25, a ventricular heartbeat sensor 35, and a telemetry circuit 30. The preferred embodiment of the pace and sense circuit 17 includes an impedance measurement circuit 14 for measuring impedance within heart 11 as an indication of a physiological parameter corresponding to the patient's metabolic demand. The pace and sense circuit 17 further includes a control block 39 which provides interfacing with the microprocessor 19.

In operation, the atrial and ventricular heartbeat sensor circuits 25 and 35 detect respective atrial and ventricular analog signals 23 and 33 from the heart 11 and convert the detected analog signals to digital signals. In addition, the heartbeat sensor circuits 25 and 35 receive an input atrial sense control signal 27 and an input ventricular sense control signal 37, respectively, from the control block 39 which determines the sensitivities of the sensor circuits. The sensitivity determines the minimum voltage deviation required at a sensing electrode for a sense to be registered, i.e., a depolarization signal to be recognized by the pacemaker.

The atrial pacing pulse generator circuit 34 receives from the control block 39, via an atrial pacing control bus 28, an atrial pace control input and an atrial pacing energy control input to generate an atrial pacing pulse 22 at appropriate times. Similarly, the ventricular pacing pulse generator circuit 34 receives from the control block 39, ventricular pace control signals on control bus 38 and pacing energy control input 48 to generate a ventricular pacing pulse 32. The atrial and ventricular pace control inputs determine the respective types of atrial and ventricular pacing that take place, while the atrial and ventricular pacing energy control inputs determine the respective magnitudes of the pulse energies.

The pacemaker 10 makes an impedance measurement when the microprocessor 19 sends via communication bus 42 a signal on the impedance control bus 21 to activate the impedance measurement circuit 14. The impedance measurement circuit 14 then applies a current to the ventricular cardiac lead 13 and measures a voltage resulting from the applied current to determine an impedance indicative of the metabolic demand of the patient.

The telemetry circuit 30 provides a bidirectional link between the control block 39 of the pace and sense circuit 17 and an external device such as a programmer. It allows data such as various operating parameters to be read from or set in the implanted pacemaker. An exemplary programmer is the 9600 Network Programmer manufactured by Telectronics Pacing Systems, Inc. of Englewood, Colo., U.S.A.

Figure 3:
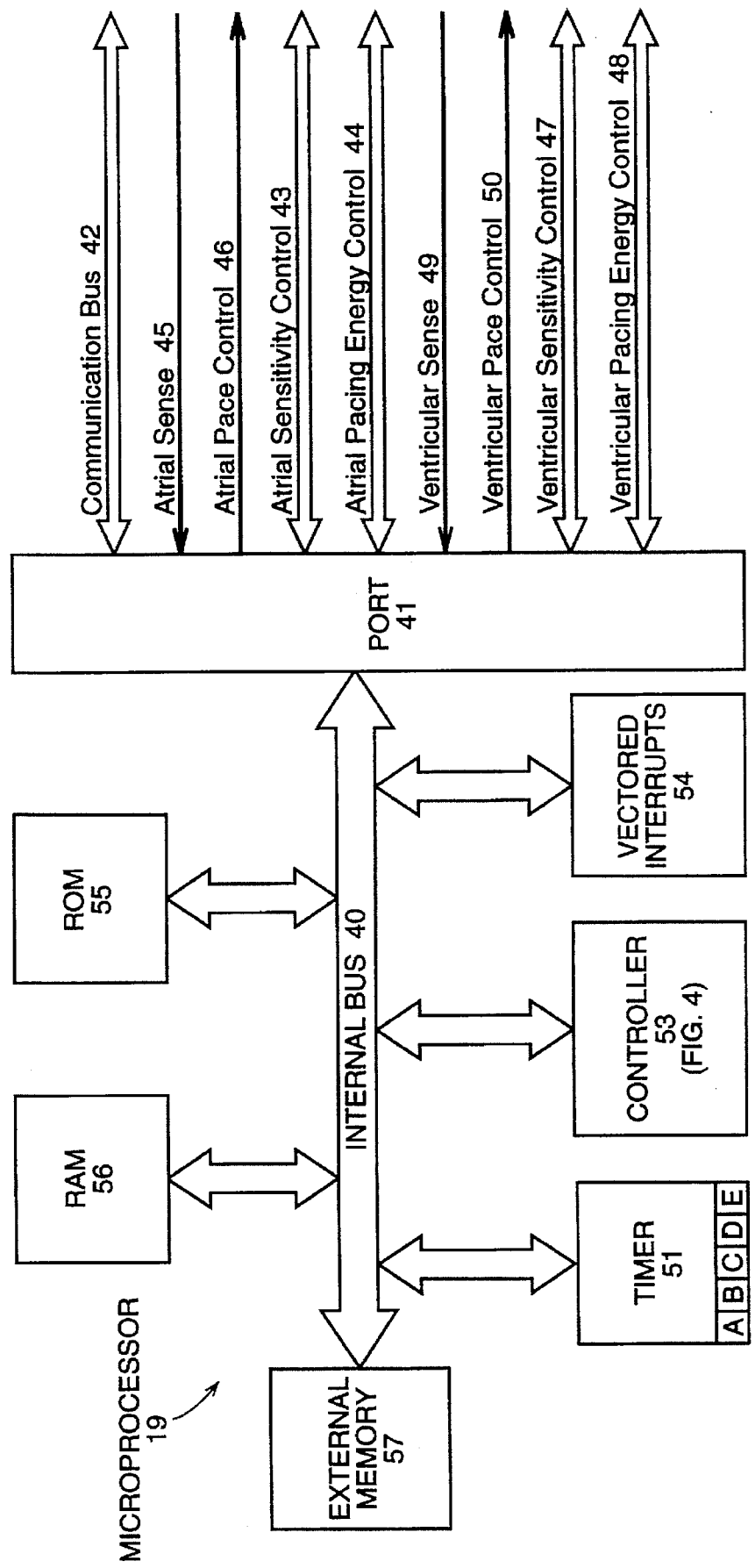
FIG. 3 shows a block diagram of the microprocessor for the pacemaker of FIG. 1.

FIG. 3 shows the microprocessor 19 having a timer circuit 51 which may include multiple individual 16-bit timers, a controller 53, a vectored interrupts circuit 54, a ROM 55, a RAM 56, an external memory 57 and an interface port 41. Signals between these elements are exchanged via an internal communications bus 40. Timer circuit 51 generates various timing signals at its output ports A–E as shown in FIG. 3. The RAM 56 acts as a scratchpad and active memory during execution of the programs stored in the ROM 55 and used by the microprocessor 19. ROM 55 is used to store programs including system supervisory programs, detection algorithms for detecting and confirming arrhythmias, and programming for determining the rate of the pacer as described below, as well as storage programs for storing, in external memory 57, data concerning the functioning of the pulse generator 10 and the electrogram provided by the ventricular cardiac lead 13. The timer circuit 51, implements timing functions required by the microprocessor 19 without resort entirely to software, thus reducing computational loads on, and power dissipation by, the controller 53.

Signals received from the telemetry circuit 30 permit an external programmer (not shown) to change the operating parameters of the pace and sense circuit 17 by supplying appropriate signals to the control block 39. The communication bus 42 carries these signals to the microprocessor 19.

The microprocessor 19 through its port 41 receives status and/or control inputs from the pace and sense circuit 17, such as the sense signals on the sense lines 45 and 49. It performs operations, including arrhythmia detection, and produces outputs, such as the atrial pace control on the line 46 and the ventricular pace control on the line 50, which determine the type of pacing that is to take place. Other control outputs generated by the microprocessor 19 include the atrial and ventricular pacing energy controls on the buses 44 and 48, respectively, which determine the magnitude of the pulse energy, and the atrial and ventricular sensitivity controls on the buses 43 and 47, respectively, which set the sensitivities of the sensing circuits. Importantly, the rate of atrial and ventricular pacing is adjusted by controller 53, as set forth below, to compensate for changes in the physical activity of the patient.

The pacemaker 10 of the present invention will function properly using any metabolic indicator rate system, so long as that system is able to reliably relate the sensed parameter to a metabolic demand pacing rate. For example, U.S. Pat. No. 4,766,901 to F. Callaghan, issued Aug. 30, 1988 for "Rate Responsive Pacing System Using the Integrated Evoked Potential" refers to the operation of a rate-responsive pacing system using the integrated evoked ventricle depolarization potential as a metabolic demand pacing rate indicator. U.S. Pat. No. 4,702,253 to T. A. Nappholz et al., issued Oct. 27, 1987 for "Metabolic-Demand Pacemaker and Method of Using the Same to Determine Minute Volume," U.S. Pat. No. 4,901,725 to T. A. Nappholz et al., issued Feb. 20, 1990 for "Minute Volume Rate-Responsive Pacemaker", and U.S. Pat. No. 5,201,808 to B. M. Steinhaus et al, entitled "Minute Volume Rate-Responsive Pacemaker Employing Impedance Sensing on a Unipolar Lead", which issued on Apr. 13, 1993, disclose rate responsive pacers using another metabolic demand pacing rate indicator, respiratory minute volume, as the rate control parameter. The subject pacemaker can use any of the metabolic indicated rate responsive techniques described in these and numerous other patents. The above-mentioned patents are therefore incorporated herein by reference. The preferred embodiment of the invention employs an impedance sensor 14, shown in FIG. 2, which performs an impedance measurement to determine the respiratory minute volume in accordance with the '725 Nappholz et al. patent.

Figure 4:
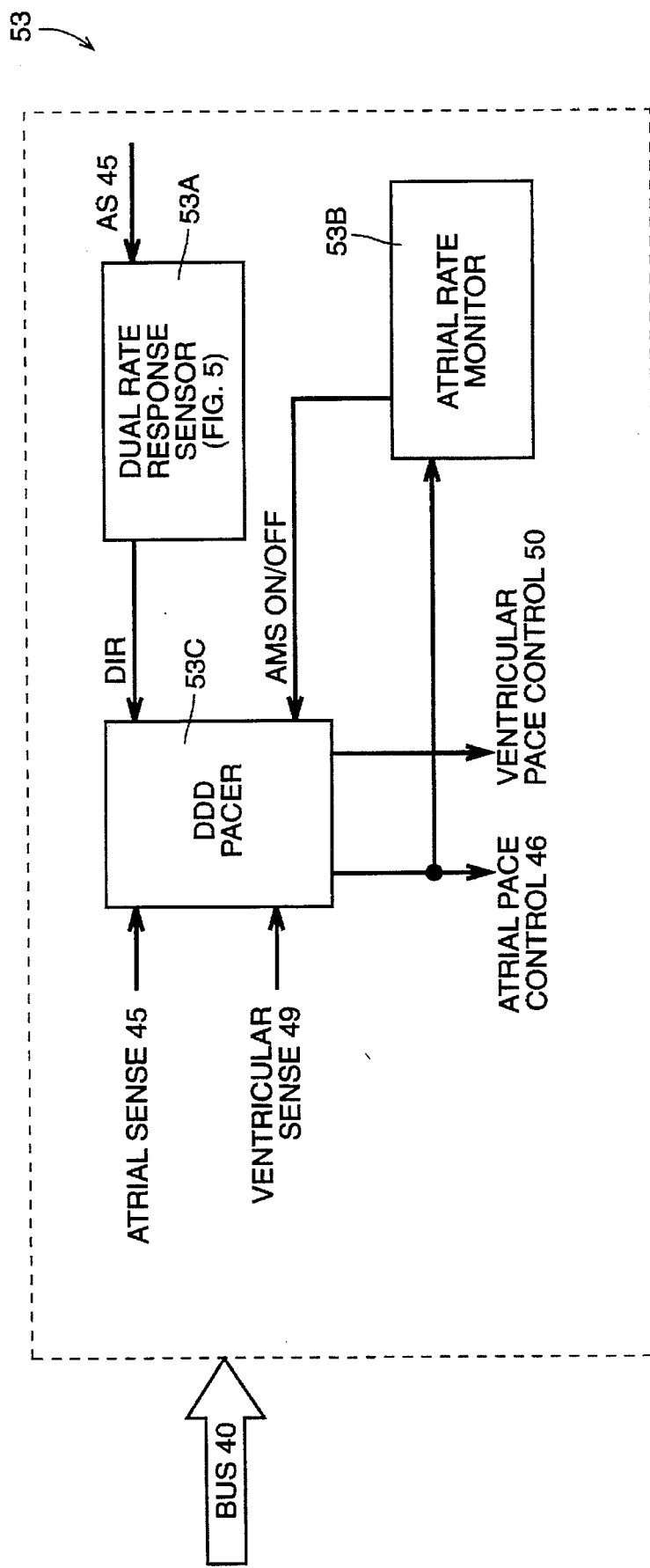
FIG. 4 shows a block diagram of the controller for the microprocessor of FIG. 3.

FIG. 4 shows the functional block diagram of the controller 53 of FIG. 3. The dual rate responsive sensor 53A generates the Dual Sensor Indicated Rate (DIR) signal which is used by the pacing and sensing system (shown symbolically as the DDD pacer block 53C in FIG. 4) to determine the length of each of the intervals used in the timing cycle. The atrial rate monitor 53B generates an Automatic Mode Switching (AMS) signal upon detection of a non-physiological atrial rate and rhythm. This AMS signal automatically switches the pacemaker to a ventricular pacing mode, where atrial pacing is temporarily disabled. When a physiological atrial rate resumes, the AMS signal is deactivated and the pacemaker returns to an atrial tracking mode.

Figure 5:
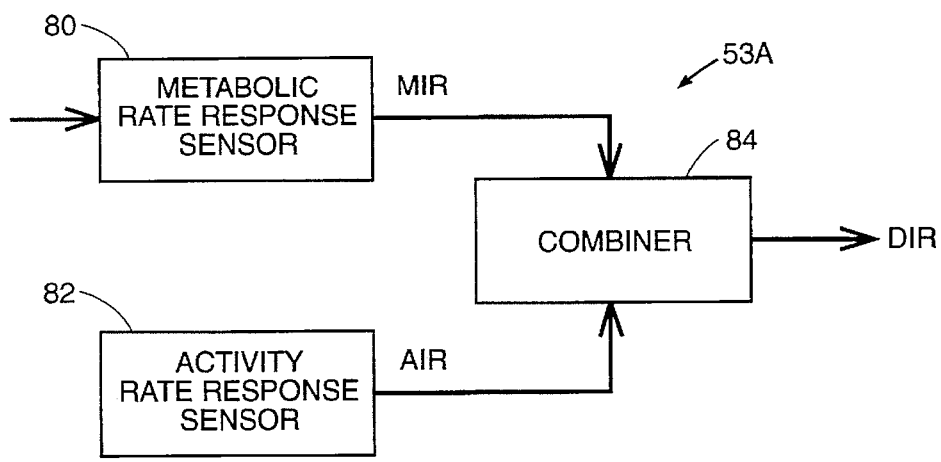
FIG. 5 shows a block diagram of the dual rate responsive sensor for the controller of FIG. 4.

The following description pertains to the elements and operations associated with adjusting the pacer rate to compensate for the physical activities of the patient using both an activity and a metabolic response rate. As shown in FIG. 5, the dual rate responsive sensor 53A consists of a metabolic rate response sensor 80 and an activity rate response sensor 82. The metabolic rate responsive sensor 80 may be, for example, a minute volume variation type sensor retrieving data supplied by internal bus 40 and the communication bus 42 from the impedance measurement 14 (FIG. 3). Sensor 80 generates a minute volume signal based on the impedance sensed by impedance measurement circuit 14. The minute volume signal in turn is mapped into a metabolic indicated rate (MIR).

Figure 6:
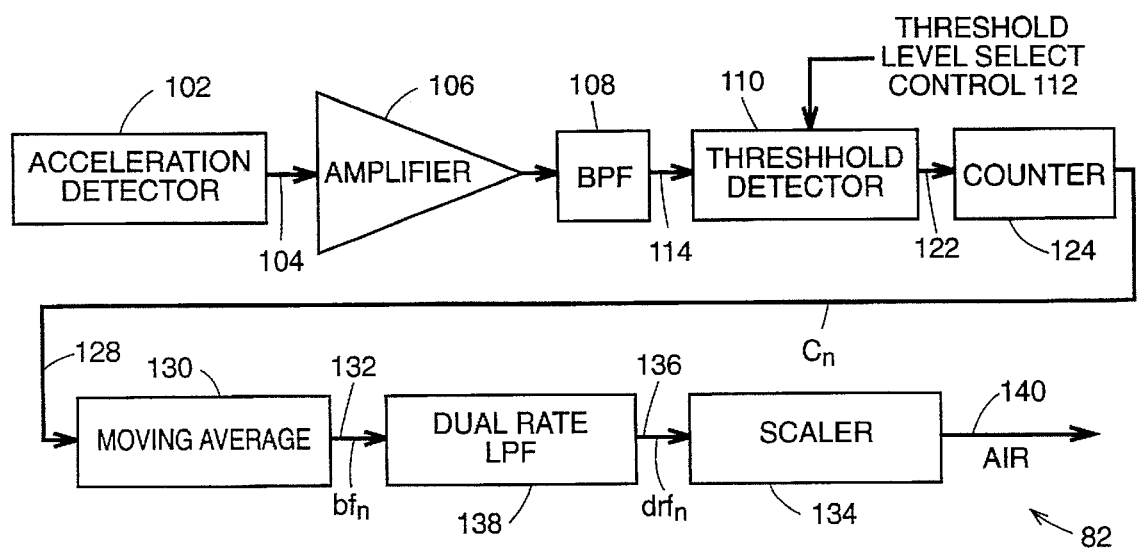
FIG. 6 shows a block diagram for an activity rate responsive sensor for the dual sensor of FIG. 5.
Figure 7:
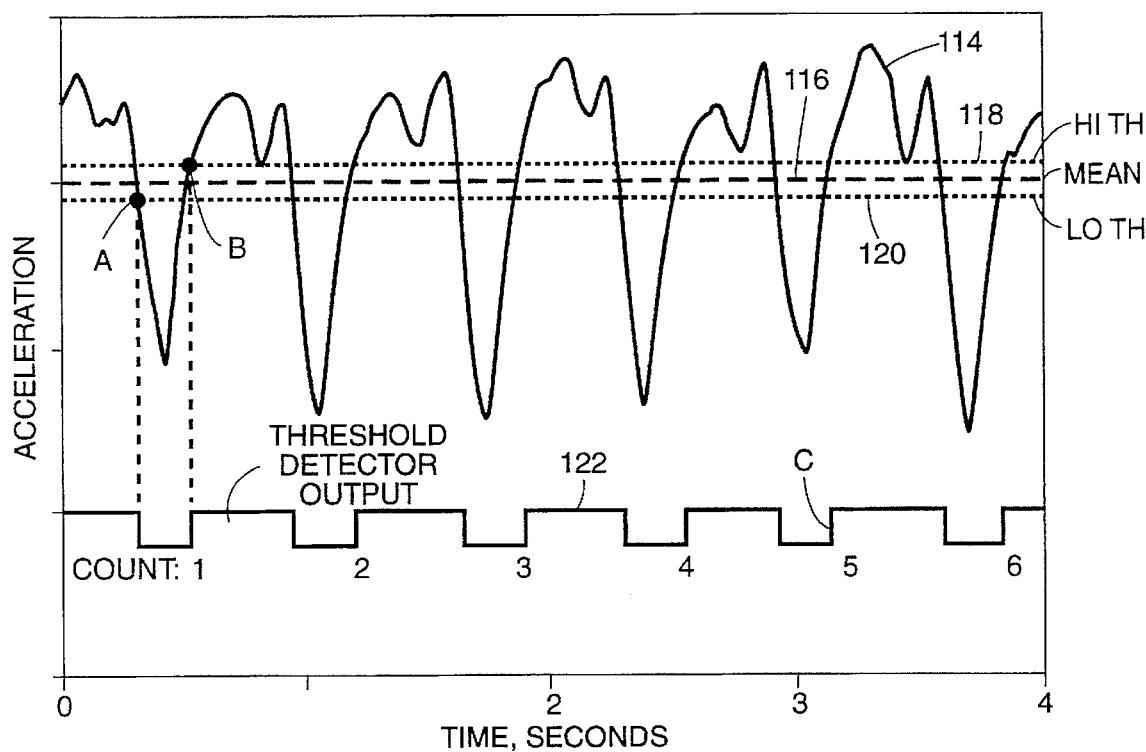
FIG. 7 shows a chart of the acceleration signal developed in the sensor of FIG. 6.
Figure 8:
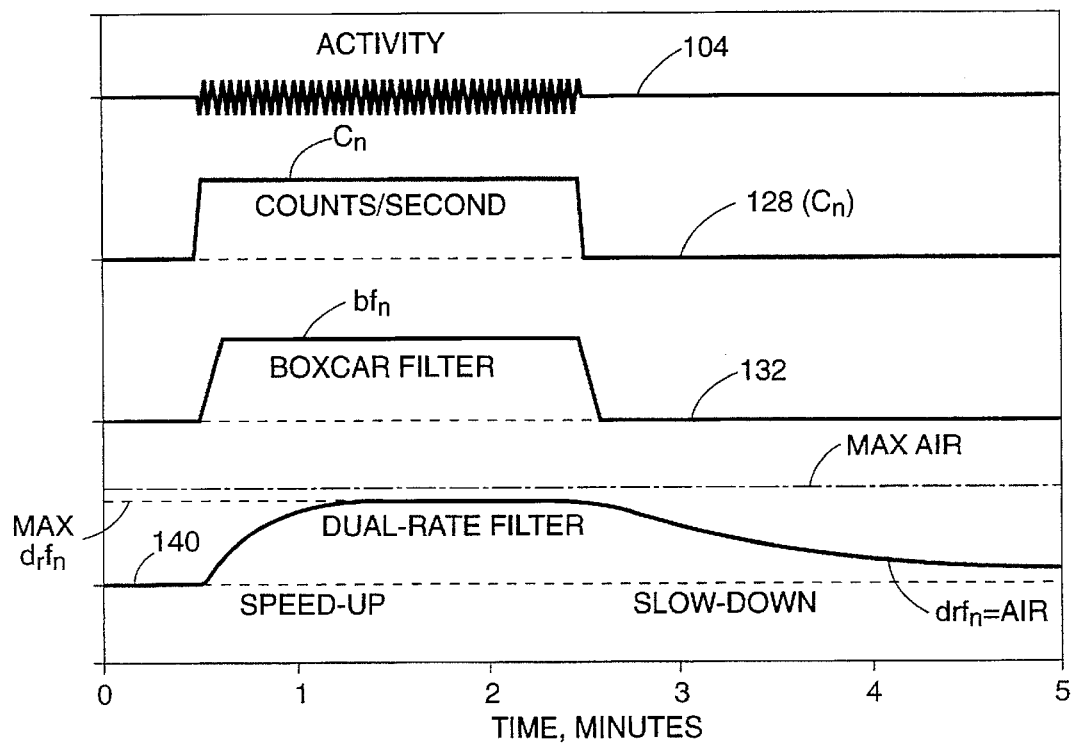
FIG. 8 shows curves for various signals generated within the activity rate response sensor of FIG. 6.

The activity rate response sensor 82 may be, for example, an acceleration type sensor, shown and characterized in FIGS. 6–8, which generates a signal AIR (Activity Indicated Rate). This sensor 82 may include an acceleration detector 102 (FIG. 6) which detects a patient's body movements during exercise and generates a corresponding electrical signal on line 104. Typically, all the components of the pacemaker described above are disposed in a low profile housing (not shown) having two facing flat surfaces and are mounted on a common substrate within said housing. Preferably, the detector 102 is mounted on the common substrate and is sensitive to accelerations normal to the flat surfaces of the housing. Detector 102 may be, for example, a piezoelectric ceramic accelerometer such as Model 12M2 made by Endevco of San Juan Capistrano, Calif. and may be responsive to accelerations having a frequency in the range of 1–100 Hz. Typically, the mechanical resonances of sensor and the housing are above this range. Preferably, the sensor 82 is mounted on a PCB inside the housing so that it is unaffected by the housing resonance.

The output of the accelerometer detector 102 is fed on line 104 to an amplifier 106 which raises the level of the accelerometer detector signal to a level sufficient for further signal processing. The signal output by amplifier 106 is fed to a band-pass filter 108. Filter 108 filters the amplified signal to reject signals outside a range of 1–4 Hz. This filter 108 discriminates between acceleration signals related to the sinus rate of normal patients when exercising, and other signals.

The filtered signal 114 from filter 108 is fed to a threshold detector 110. This detector 110 generates a binary signal 122 dependent on whether the output of filter 108 is above a high threshold level HITH or below a low threshold level LOTH. These levels are set symmetrically above and below the mean (or DC offset) output of the filter 108. In other words:

$$HITH = MEAN + KTH \quad (1)$$

$$LOTH = MEAN - KTH \quad (2)$$

The threshold constant KTH is selected from a look-up table based on a threshold level selector control signal 112. The threshold level is one of the parameters set by the physician when the pacemaker is initially programmed. For an accelerometer having a sensitivity of 3.64 mV/g, typical threshold constants KTH are shown below, expressed in mg or µV for the various settings available to the physician:

TABLE I

| THRESHOLD LEVEL | KTH-mg peak | KTH-µV peak |
| --- | --- | --- |
| LOW | 6.1 | 22.0 |
| MEDIUM/LOW | 8.6 | 31.1 |
| MEDIUM (nominal) | 12.1 | 44.0 |
| MEDIUM/HIGH | 17.1 | 62.2 |
| HIGH | 24.2 | 88.0 |

In FIG. 7, the mean filter output is indicated by a horizontal line 116, the low threshold level LOTH by line 120 and the high threshold level HITH by line 118. When the filter output signal 114 drops below LOTH (as at A), the threshold detector output 122 drops to a low level. When signal 114 rises above HITH, as at B, the threshold detector output 122 goes high as shown in FIG. 7.

The output 122 of detector 110 is fed to a counter 124 which counts the number of positive transitions (such as C in FIG. 7) during a preset time period, for example 1.5 seconds. The output $C_n$ of counter 124 is fed to a moving average filter 130 which averages the last N counts $C_n$. The filter 130 is provided as a smoothing or integrating means to eliminate spurious acceleration signals. More specifically, filter 130 generates an output $bf_n$ on line 132 which is the sum of the last N counts $C_n$ where N may be, for example, five. Thus $bf_n$ may be represented as:

$$bf_n = \sum_{n-N}^{n} C_n \quad (3)$$

Of course, strictly speaking, the average of the last N counts $C_n$ is $bf_n/N$. However, since the filter 130 is used as a smoothing means, and since its output needs proportional scaling anyway, the division by N may be omitted.

In a healthy person, as increased physical activity is initiated, the patient's heartbeat builds up gradually from an initial, or rest rate toward a maximum rate. Similarly, when the physical activity ceases, the heartbeat slows down gradually from the maximum rate toward the rest rate. This natural function is implemented in the sensor 82 using the dual rate low pass filter 138. Importantly, it has been found that the time constant during buildup is much faster than during slow down. Accordingly, the dual rate filter 138, as the name implies, is designed with two time constants, namely, a first time constant for the initial build up and a second, much slower ending time constant for the slow down phase. The build up time is the time required to build up the heart rate to 90% of its final or maximum value while the slow down time is the time required for the heart beat to decay by 90% from its maximum value.

More specifically, dual rate filter 138 generates an output $drf_n$ which is related to its previous output and its input bfn as follows:

for the build up phase, $$\text{if } bfn > drf_{n-1} \quad drf_n = drf_{n-1} + k1*(bfn - drf_{n-1}) \quad (4)$$

for the slow down phase, $$\text{if } bfn < drf_{n-1} \quad drf_n = drf_{n-1} + k2*(bfn - drf_{n-1}) \quad (5)$$

The constants k1 and k2 are the two time constants discussed above, established empirically for patients dependent on age, sex, weight, physical condition and so on for various build up and slow down times.

Some typical values for k1 and k2 are given below with the preferred or nominal values also being indicated:

TABLE II

| BUILD UP TIME (MINUTES) | k1 |
| --- | --- |
| 0.25 | 0.206 |
| 0.5 (nominal) | 0.109 |
| 1.0 | 0.0556 |

TABLE III

| SLOW DOWN TIME (MINUTES) | k2 |
| --- | --- |
| 2.5 (NOMINAL) | 0.0228 |
| 5 | 0.0115 |
| 10 | 0.0057 |

As can be seen from these tables, time constant k2 is an order of magnitude smaller than time constant k1, indicating that the output of filter 138 is much slower at the end of exercise than at the exercise onset.

Preferably the filter 138 further sets a maximum value for its output $drf_n$ (maxdrf) which cannot be exceeded.

Typical curves for the output of the counter 124 ($C_n$), moving average filter ($bf_n$) and dual rate low pass filter ($drf_n$) developed by the activity rate response circuit 82 for a constant physical activity of about 2 minutes are shown in FIG. 8.

Figure 9:
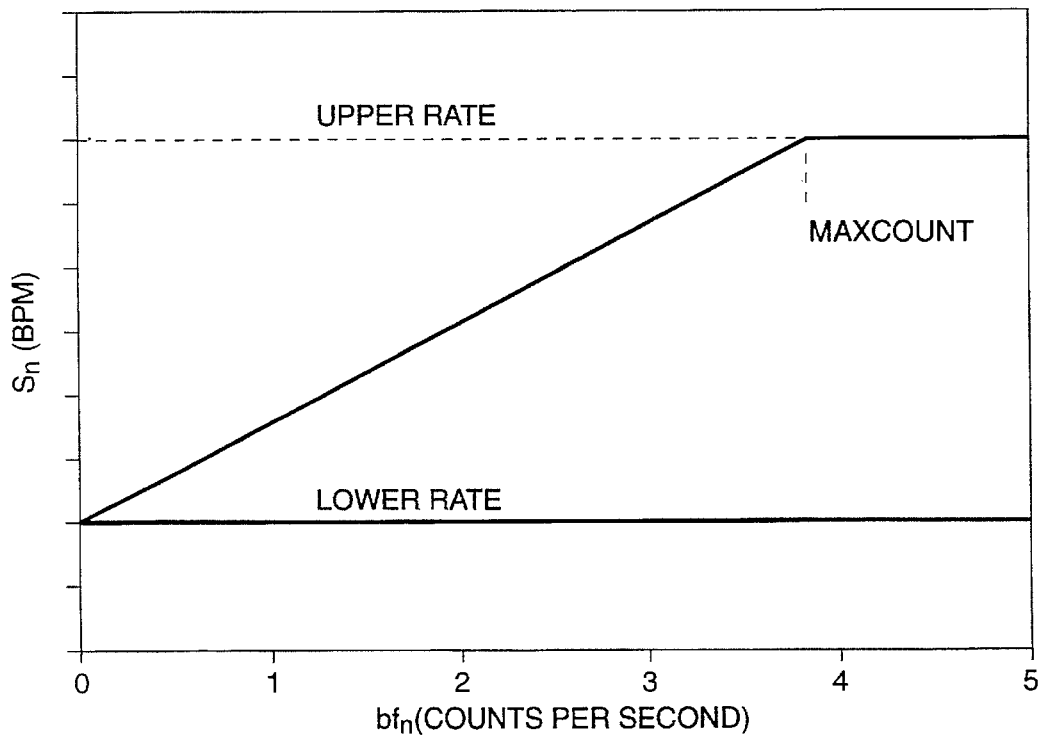
FIG. 9 shows the conversion performed by the scaler used in the activity rate response sensor of FIG. 6.

The output drfn is fed to a scaler 134. Scaler 134 multiplies its input by a constant scaler factor as described below to obtain a scaled output on line 136. More particularly, the output drfn (which after filtering is still in counts per second) is converted to a pulse rate in beats per minute, as shown in FIG. 9.

The output of the scaler 134 on line 140 is the overall resultant Activity Indicated Response AIR of sensor 82. This signal must be compatible with the output MIR of the metabolic rate response sensor 80. This is accomplished by adjusting the scaling constant in scaler 134 so that the maximum level of AIR (max drf) equals the maximum level of MIR.

It should be understood that while the elements of sensor 82 are shown as discrete elements, for the sake of clarity, most of them, including counter 124, scaler 134, and filters 132 and 138 are implemented by software in the microprocessor 19.

As shown in FIG. 5, the two rate responses MIR, AIR are fed to a combiner circuit 84 which combines the responses into a Dual Sensor Indicated Rate (DIR) signal.

In the following description, various embodiments of the combiner circuit 84 are provided. It should be understood that these embodiments may be used to operate on or combine any metabolic indicated rate signal MIR and any activity indicated rate signal AIR. The AIR signal may be the signal from the acceleration rate sensor 82 or any other type of circuit which generates a signal by sensing an actual physical activity. As previously mentioned, a problem with all present systems using a metabolic indicated rate is that the metabolic parameter used changes at a rate which is too slow. Since the activity indicated rate (AIR) rises much faster than the metabolic rate, in the present invention, the activity rate (AIR) is monitored. As a rapid rate increase is detected in the activity indicated rate (AIR), the AIR signal is used to boost the MIR signal. The boosted signal is the DIR signal produced by combiner 54. Various boosting schemes used to implement the chamber are shown in FIGS. 10–15 and described below. As indicated in the various embodiments, the purpose of the present invention is to boost the MIR signal at the exercise onset, when it is important to provide the patient with sufficient oxygen. At the end of the exercises the MIR still lags however since results only in a slightly more oxygen to the patient which is not harmful and therefore no correction may be required.

Figure 10:
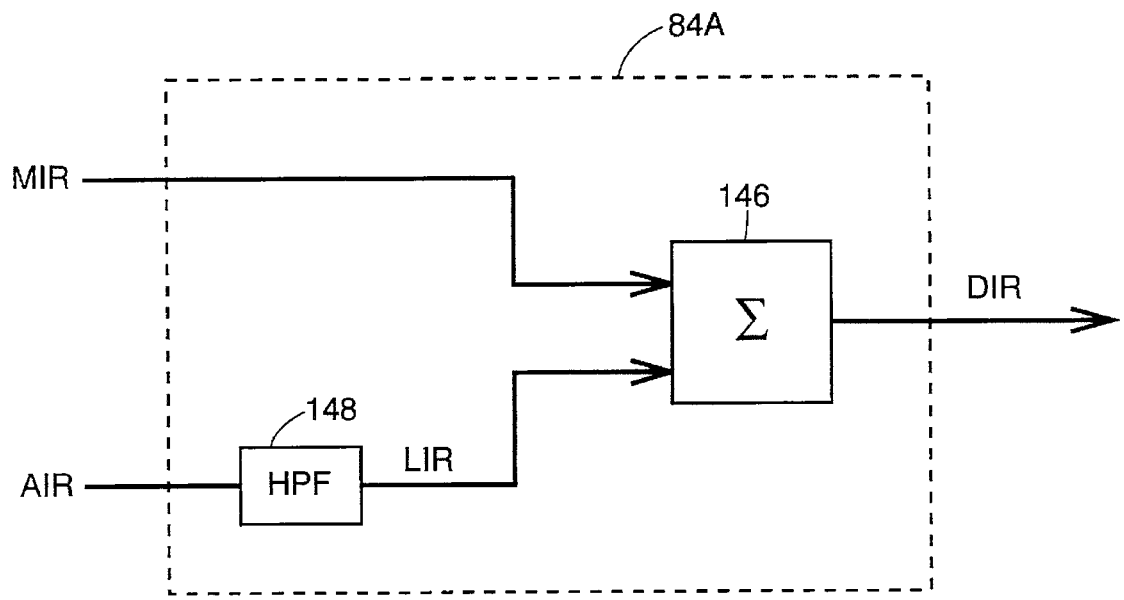
FIG. 10 shows a first embodiment of the combiner for the dual sensor of FIG. 5.

In FIG. 10, an embodiment is shown wherein combiner 84A consists of a summing circuit 146 and a high pass filter 148 for generating a lead indicated rate LIR. Signal LIR is indicative of a transition in the AIR signal, and therefore in the level of physical activity of the patient.

Signal LIR is fed to circuit 146 for summing with MIR, the circuit 146 generating the DIR output signal. Thus, the response of circuit 84A during the transition periods is given by $$DIR = MIR + LIR. \quad (6)$$

Once a steady state has been achieved the output of filter 148 goes low and the output of the circuit becomes:

$$DIR = MIR. \quad (7)$$

As previously mentioned, the metabolic response indicated rate MIR lags substantially being the physical activity level. Therefore, in this embodiment, during the exercise onset period, the high frequency components of AIR and forming the signal LIR boosts the MIR signal.

Figure 11:
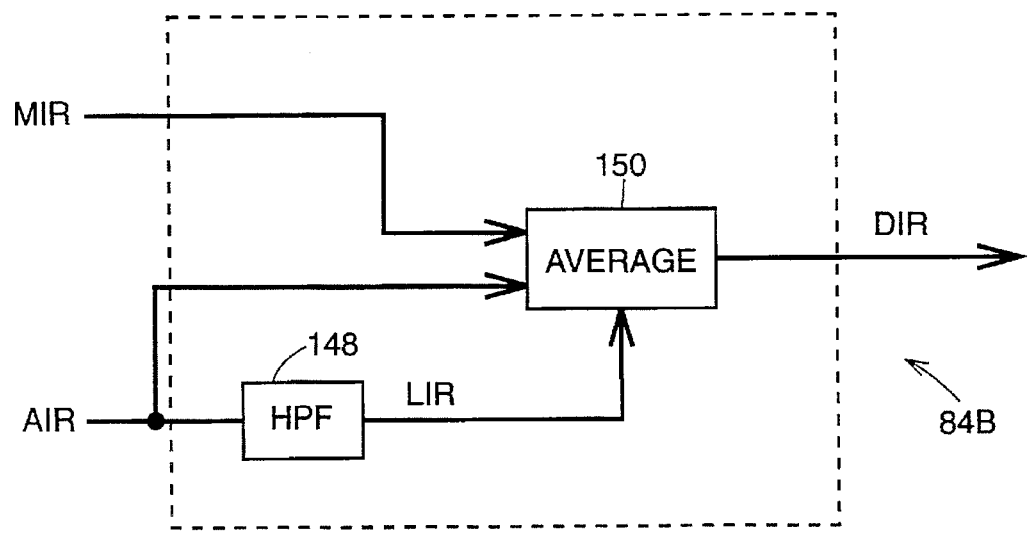
FIG. 11 shows a second embodiment of the combiner for the dual sensor of FIG. 5.

In the embodiment of FIG. 11, the combiner circuit 84B consists of a high pass filter 148 identical to filter 148 in FIG. 10, and an averaging circuit 150. The signals MIR and AIR are generated in real time by circuitry disposed for extended time periods in the patient's body. Therefore at various instances of time, it is expected that one or the other of these signals experiences noise, emanating dropouts, surges, hyperventilation, and so forth. These effects are significantly reduced by the averaging circuit. As mentioned above, during steady state conditions, the output of the high pass filter 148 is low and the circuit 150 generates signal DIR which is the arithmetic average of AIR and MIR. Like in the embodiments of FIG. 10, during the transition the circuit 150 boosts the signal DIR thereby compensating for the lag of MIR.

Figure 12:
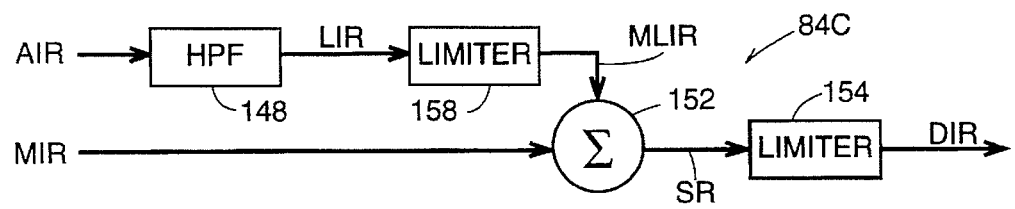
FIG. 12 shows a third embodiment of the combiner for the dual sensor of FIG. 5.

FIG. 12 shows a further modification of the embodiment of FIG. 10. This embodiment is provided to handle very fast transitions from a rest mode to a full exercise mode. In this embodiment, the combiner circuit 84C includes high pass filter 148, a first limiter 158, a summing circuit 152 and a second limiter 154. The high pass filter 148 generates a signal LIR as discussed above, indicative of transitions in the physical activity level of the patient. During initialization, the maximum (R max) and the minimum (R min) rates for pacing are set. The difference between these rates is a parameter M. Limiter 158 clips the signal LIR so that this signal does not exceed R min by more than 50% of M. Signal LIR is further lipped by limiter 158 so that it is never negative. This limited signal MLIR is fed to summing circuit 152. Just as in the embodiment of FIG. 10, MIR is boosted by the LIR signal during transitions. The major improvement in this embodiment is the use of the limitations to insure that (1) DIR does not rise too fast, and (2) that DIR does not exceed its maximum permissible limits. During steady state conditions, output SR is equal to MIR. To insure that the output SR is not excessive, limiter 154 clips it to the level M as defined above. The clipped output LMIR of limiter 154 is fed to a cross check circuit 156 where a final check is performed to insure that if the patient is not involved in a strenuous activity than a high pacer rate is not generated even if the signal MIR is high, as discussed below.

Typical curves for signals AIR, MIR, LIR and the Dual Rate Indicated signal DIR obtained by using the circuit of FIG. 10 are shown in FIG. 13 for a patient exercising for a three minute period, with the ordinate being normalized. The signal DIR fed to the DDDR pacer circuit is very similar to the natural heart beat rate of a normal person doing the same exercise.

As can be seen from FIG. 13, during the onset of the exercise period (first minute), the signal DIR is close to but always somewhat smaller than the signal AIR, thus ensuring that the rate response during this period is relatively fast but not so fast as to become too drastic a change. As the higher level steady state of activity is achieved, the signal DIR approaches the metabolic rate MIR. During the termination period, the signal DIR follows AIR, but again it does not change as fast as MIR.

Figure 14:
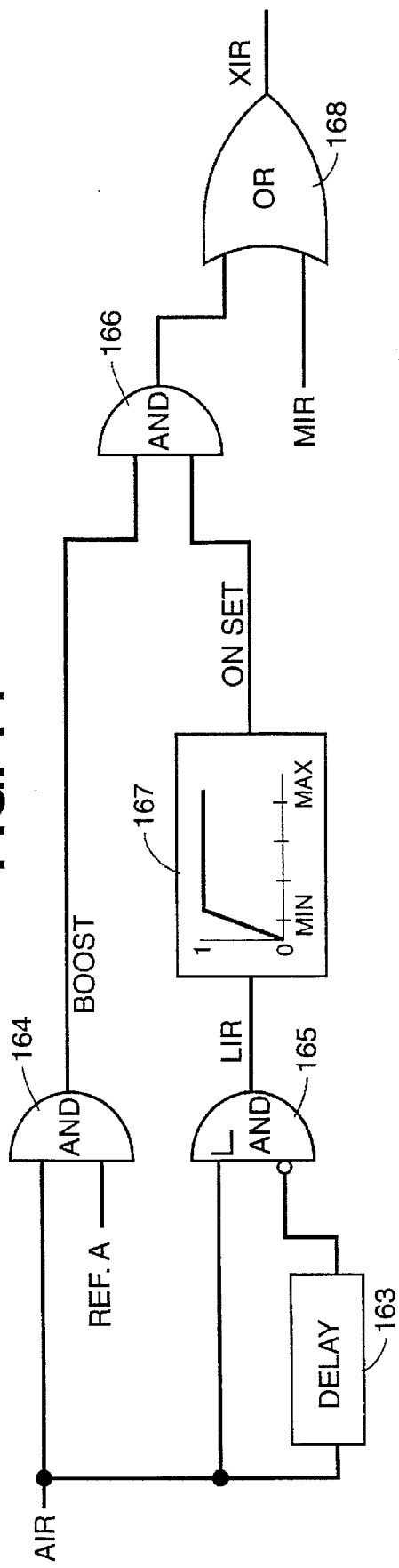
FIG. 14 shows a time chart of various signals typical for the embodiment of FIG. 12.
Figure 15:
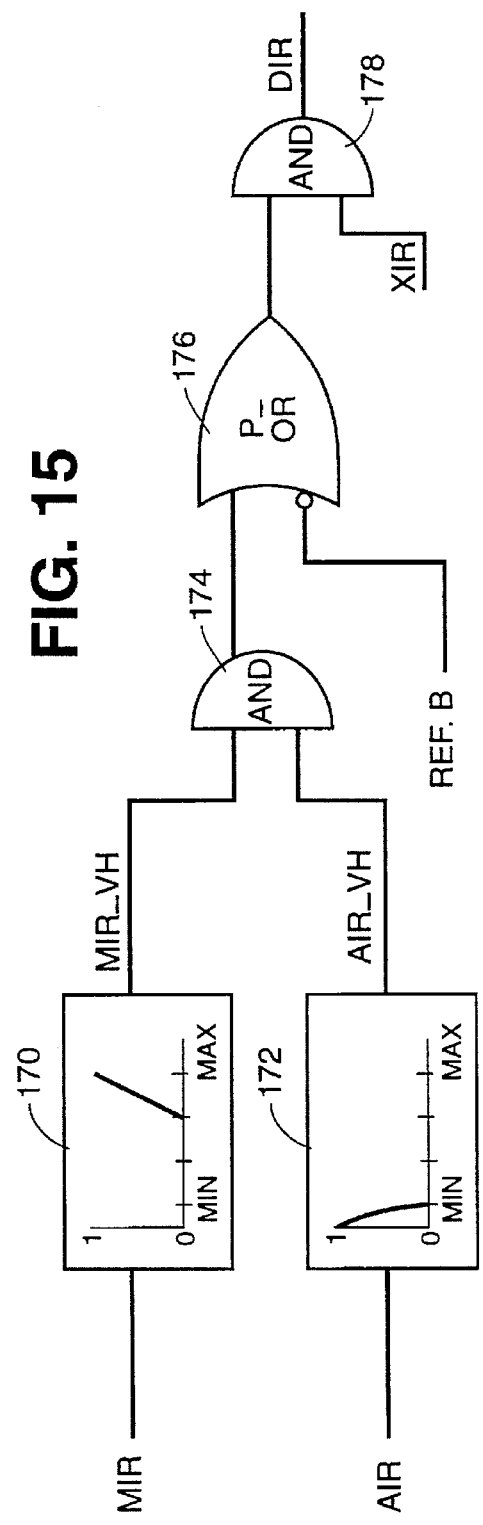
FIG. 15 shows a fourth embodiment of the combiner for the dual sensor of FIG. 5.

In order to insure that the output DIR is controlled to operate safely, in a somewhat preferred embodiment shown in FIGS. 14 and 15 the combiner is implemented so that it follows a set of mutually exclusive rules. More specifically, the output of the combiner is defined by the following rules:

Rule 1: If the metabolic indicated rate is near its maximum level and the activity indicated rate is near its minimum then the output dual indicated rate cannot exceed R min by 25% of M. This rule is essentially a cross-checking rule. It performs a cross-check between the metabolic indicated rate and the activity indicated rate. If the former is very high while the latter is low, an abnormal condition is assumed and DIR is not allowed to rise very high. The safety level selected in this rule is 25% of the total allowable elevation M above the rest or minimum rate R min.

Rule 2: The activity indicated rate cannot boost the output signal DIR above 50% M. This rule is another safety feature used to insure that the DIR does not run away in response to rigorous exercise, or possibly other artifacts detected by the activity indicated rate sensor.

Rule 3: During onset of exercise, the output signal DIR should be boosted to the level of the activity indicated rate. This rule is similar to the previous embodiment in that it provides for the boosting of the metabolic indicated rate (see Rule 4) during exercise onset. In this manner, the initial lag in the metabolic indicated rate is effectively eliminated.

Rule 4: Subject to Rules 1–3, the output signal DIR follows the metabolic indicated rate. This is the default or normal operation of the combiner. It is expected that most of the time the combiner essentially is idle and the DIR signal just follows MIR. The MIR signal is boosted, under Rule 2, at the onset of exercise to compensate for or essentially eliminate the lag in the metabolic indicated rate during this time. For the sake of safety, the boosting is limited by Rule 3. Rule 1 is more of an overseeing function which protects the system from abnormalities.

These rules have been implemented as an expert system using the fuzzy logic circuit elements shown in FIGS. 14 and 15. In these figures conventional logic gates such as inverter, AND, OR and P_OR gates are used to represent the following functions:

AND (A, B) or AB means the smallest of A and B, or min (A, B);

OR (A, B) or A+B means the largest of A and B, or max (A, B);

P_OR (A, B) means A+B−AB

L_AND(A, B) means max (A+B−1, 0); and

NOT A means 1−A.

In addition, special membership function gates are used to implements certain preselected fuzzy logic rules, as described below.

FIG. 14 is used to implement Rules 2 and 3. In this Figure, signal AIR is fed to an AND gate 164. The other input to this gate is a reference signal REF. A. Preferably REF. A is set so that it is at 50% of M above R min. For example, if for a person the minimum and maximum rates of DIR are:

R min=60 pps and

R max=160 pps

M=R max−R min=100

Therefore REF A=R min+M/2=110.

At the beginning of exercise, as AIR rises, the output BOOST of gate 164 follows the AIR until AIR reaches REF. A. For the example given above, the signal BOOST is equal to AIR. When AIR exceeds REF A, the output BOOST remains at REF. A.

FIG. 14 also shows an another embodiment for obtaining the Lead Indicated signal, LIR. This LIR signal is indicative of a transition in the level of exercise of a patient, as previously explained. In this embodiment, the signal AIR is fed to a time delay 163, which may be implemented by using a single pole low pass filter. The output of the delay is inverted and fed to an L_AND gate 165, which in effect acts as a low pass filter. the output of this gate is the LIR signal because delay 163 and gate 165 cooperate to simulate a high pass filter similar to high pass filter 148 of FIG. 10. The LIR signal is next fed to a membership function block 167. As shown in FIG. 14, this function block generates an output signal ONSET which rises from 0 to 1 proportionally as its input LIR to rises from its minimum MIN to a level of MIN+50% M. Above this latter level of LIR, the output signal ONSET remains at its high level '1'. Therefor this block 167 insures that the ONSET signal is fully responsive to LIR signals at or above MIN+50% M.

The signals BOOST and ONSET are fed to another AND gate 166. Since the signal LIR is in effect a differential signal of AIR, it, and the ONSET signal rise faster than BOOST and hence the output of gate 166 follows the BOOST signal for as long as there is an exercise transition. Once the transition is finished, the LIR and the ONSET signals drop to zero, and hence the output of gate 166 also drops to zero also. For negative transitions of LIR, which occurs at the end of the exercise period, the output of gate 166 remains clamped at zero. Thus, the gates 164 and 166 are used to implement Rules No. 2 and 3.

The output of gate 166 is fed to an OR gate 168. Gate 168 also receives the metabolic indicated rate MIR as an input. Gate 168 generates an output XIR which at the onset of exercise follows the BOOST signal until the MIR signal reaches the maximum level of BOOST. Thereafter, the output XIR of gate 168 follows MIR. Thus, gate 168 in effect implements Rule No. 4.

Referring now to FIG. 15, the cross check function defined by Rule No. 1 is implemented as follows. The MIR signal is fed to a membership function block 170 which performs the following function. For values of MIR between its minimum (MIN) and MIN+75% M the output signal MIR_VH (Very High) is low. Between values of MIR MIN+75% M and MAX, MIR_VH rises proportionally from 0 to 1, as shown. The signal MIR_VH is fed to an AND gate 174. Similarly, signal AIR is fed to a membership function gate 172 which performs the following function. For values of AIR between MIN and MIN+25% M, the block output signal AIR_VL(Very Low) drops proportionally from 1 toward 0, as shown. At higher values of MIR, MIR_VL remains low.

The output of the two blocks 170, 172 are fed to another an AND gate 174 which generates a smooth output as define above. Under normal circumstances, i.e., when the AIR and MIR track each other, one or both outputs from the blocks 170, 172 are low and hence the output of the gate 174 is also low. However, if MIR fails to track AIR but instead goes up so that it is close to MAX while AIR is still at a relative low level near MIN, the output of gate 174 goes high. This output is fed to the inverting input of a P_OR gate 176. The other input of gate 176 is connected to a REF. B. Preferably this reference is set between 20–30% of M above the minimum allowable rate MIN. For example, REF. B=R min+25% M.

Gate 176 selects at its output the higher of its inputs. As previously described, under normal conditions, the output of gate 174 is low. This output is inverted to a high and hence under normal conditions, the output of gate 176 is also high. REF. B is set to be lower than logic high. When an abnormal condition is present as described above, the output of gate 174 goes high and hence the gate 176 senses at its inverting input a low signal and hence sets its output to equal REF. B. Thus gates 174, 176 and blocks 170, 172 are used to implement Rule No. 1. The rules set forth above are hierarchical in the sense that Rule 1 takes precedence over Rule 2 and so on. Therefore in order to superimpose Rule 1 over the signal XIR (implementing Rules 2, 3 and 4) the output of gate 176 and signal XIR are fed to an AND gate 178.

Under normal conditions, the output of gate 176 is high and therefore the output DIR of gate 178 follows the signal XIR. If the abnormal conditions discussed above, namely a high MIR with a low AIR occur, the output of gate 176 goes to REF. B, i.e. R min+25% M. Under these conditions, gate 178 picks the lower of the output of gate 176 and XIR. In this manner, the output DIR is effectively clamped so that it does not exceed MIN+25% M. Hence the gate 178 superimposes the requirements of Rule 1 on Rules 2, 3 and 4.

A typical normalized time dependent profile illustrating various signals for the embodiment of FIGS. 14 and 15 for a five minute exercise period is shown in FIG. 16. During the onset of exercise, detected as a transition by the LIR signal, the DIR signal follows the AIR signal until 50% of the maximum level M is reached (point D). Thereafter the signal DIR level remains at the 50% level until the MIR signal catches up (point E). Thereafter, the DIR signal follows the MIR signal.

In this manner, the circuit of FIGS. 13 and 14 insures that its response DIR is relatively fast, much faster than MIR, however, it is not fast enough to produce a drastic change in its output, especially above 50% of the maximum rate M. In this embodiment, after DIR reaches 50% of its maximum level, it follows the signal MIR and the signal AIR is ignored. Thus the AIR signal has an effect only at the very beginning of the onset of the exercise period thereby providing a smooth, if somewhat slower response especially during the termination of the exercise.

Figure 17:
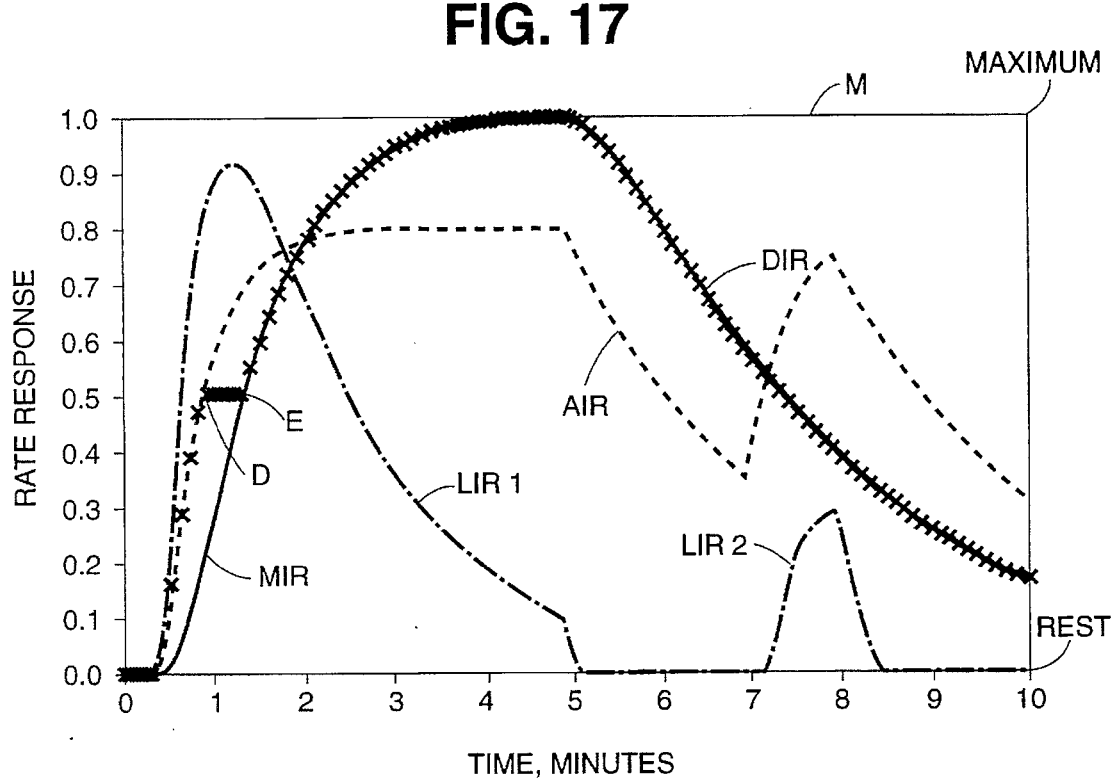

FIG. 17 shows another normalized time dependent profile generated by the embodiment of FIGS. 13 and 14 wherein an artifact caused, for example, by an environmental vibration, is detected (indicated by LIR2) after an exercise session indicated by LIR1. Since the DIR signal has not fully returned to the rest level prior to the start of the second exercise period, this artifact is ignored.

Figure 18:
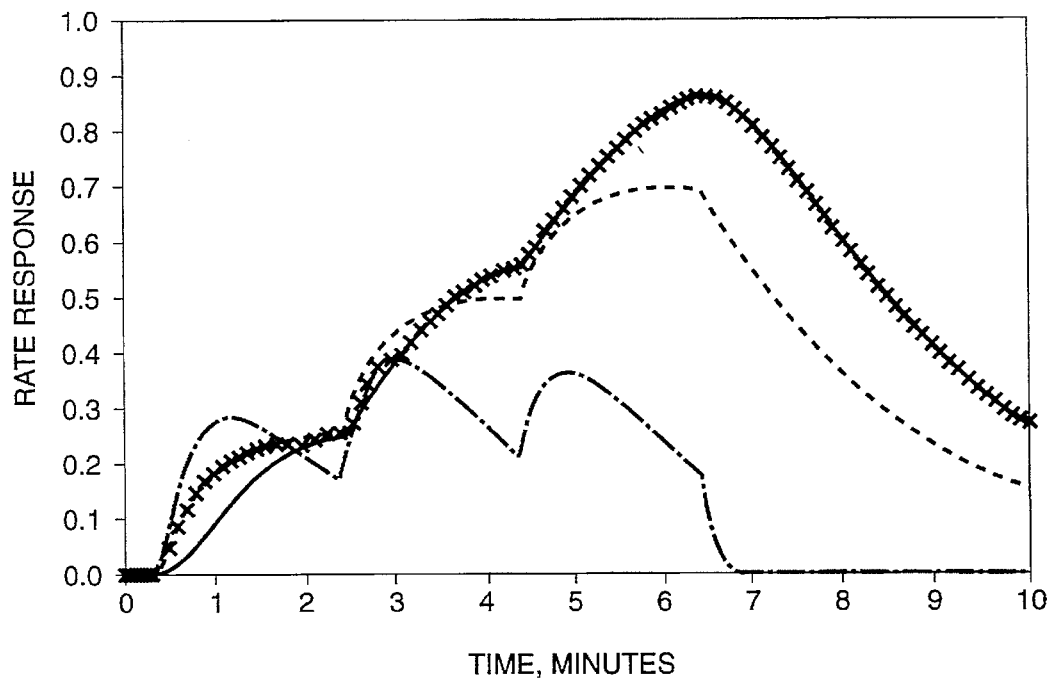

FIG. 18 shows a profile for a sequence of signal exercising periods and the corresponding signals generated by the circuit 84D.

Figure 19:
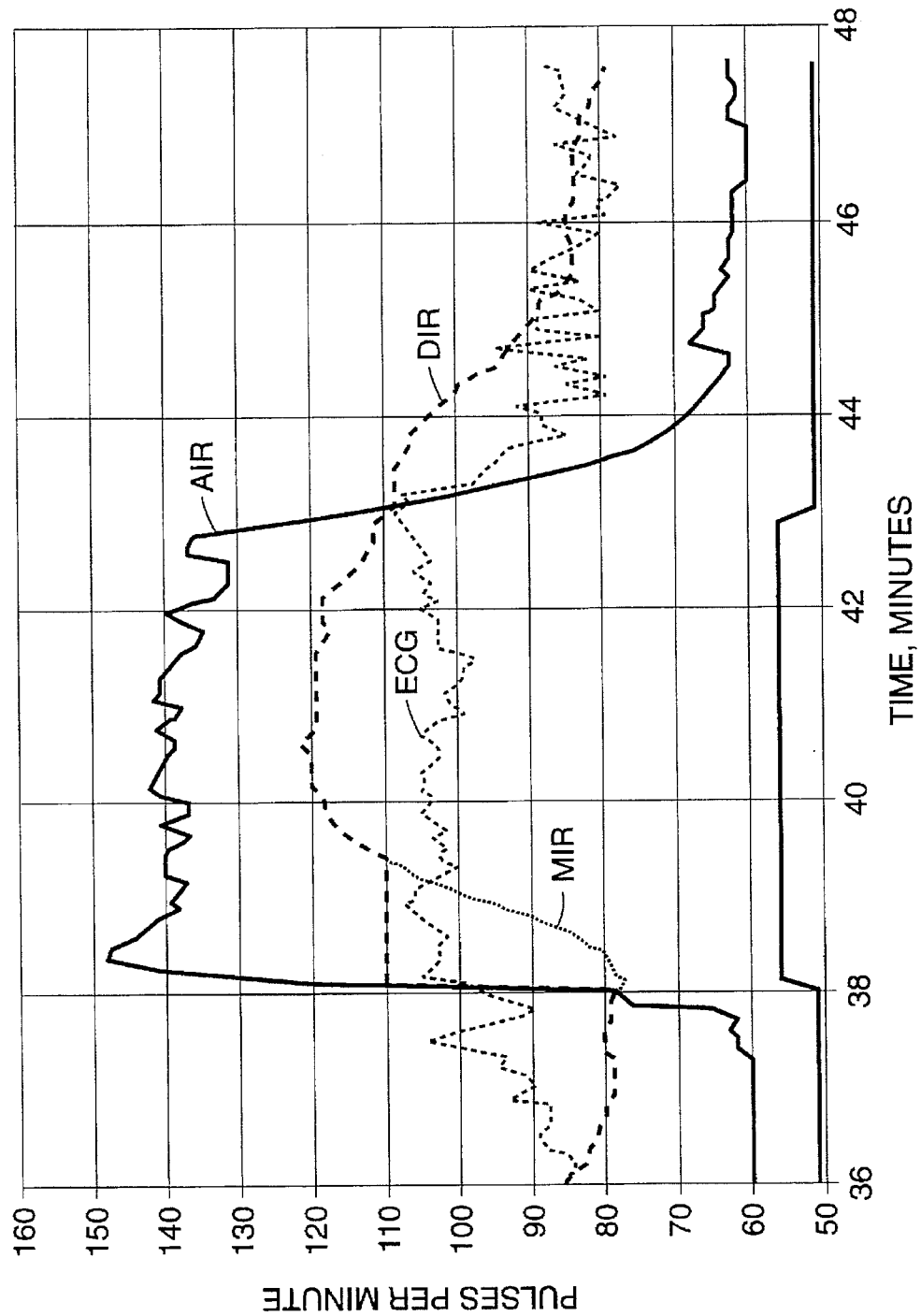

FIG. 19 shows the ECG for a person during one of a series of exercise stages together with the signals DIR and MIR that are generated for this person for artificial pacing by the subject invention as alleviated in FIG. 15. In this Figure the maximum, midrange (50% level) and minimum level rates were 160, 110 and 60 bpm respectively.

Although the invention has been described with reference to several particular embodiments, it is to be understood that these embodiments are merely illustrative of the application of the principles of the invention. Accordingly, the embodiments described in particular should be considered exemplary, not limiting, with respect to the following claims.

We claim:

1. A pacemaker comprising:
    metabolic rate sensor means for generating a metabolic indicated rate signal dependent on a physiological demand of a patient in response to a physical activity by the patient;
    activity rate sensor means for generating an activity indicated rate signal dependent on an electromechanical measurement indicative of an instantaneous parameter characteristic of said physical activity;
    combining means for generating a time dependent combined rate signal dependent on said metabolic indicated rate, said combining means including transition means for detecting a transition in said physical activity, said metabolic indicated rate being enhanced with said activity indicated rate during said transition; and
    pacing means for generating pacing signals in response to said combined rate.

2. The electronic pacemaker of claim 1 wherein said combining means further includes summing means for summing said indicated rates, said summing means generating said combined rate with said combined rate following said activity indicated rate during said transition.

3. The electronic pacemaker of claim 1 wherein said combining means includes an averaging means for averaging said indicated signals.

4. The electronic pacemaker of claim 3 wherein said transition means generates a lead signal indicative of said transition.

5. The pacemaker of claim 4 wherein said combined means further includes limiting means for limiting said lead signal to a preselected level.

6. The pacemaker of claim 5 wherein said preselected level is determined by a maximum heart rate of said patent.

7. The electronic pacemaker of claim 1 wherein said activity rate response means includes detecting means for detecting an acceleration.

8. A pacemaker comprising:
    metabolic rate means for generating a metabolic indicated rate signal dependent on a metabolic function of a patient;
    activity rate means for generating an activity indicated rate signal dependent on a physical parameter indicative of a level of physical activity of said patient;
    combining means for combining said metabolic and activity indicated rate signals into a dual rate signal, said dual rate signal being limited to a preselected maximum level, said combining means including transition means for determining a transition of said physical parameter wherein said combined means combines said signals during said transition by boosting said metabolic rate indicated signal with said activity indicated rate signal and first limiting means for limiting said activity indicated rate signal to a preselected range dependent on said maximum level; and
    pacer means for generating pacing signals responsive to said dual rate signal.

9. The pacemaker of claim 8 wherein said limiting means limits said activity indicated rate signal to a value smaller than said maximum level.

10. The pacemaker of claim 9 wherein transition means generates a transition signal when said physical parameter is in transition and wherein said combining means includes a detection circuit for detecting said transition signal.

11. The pacemaker of claim 10 wherein said combined rate signal follows said activity indicated rate when said transition signal is detected.

12. The pacemaker of claim 8 further comprising cross check means for detecting a mismatch between said indicated rate signals to limit said combined rate signal.

13. The pacemaker of claim 12 wherein said cross check means includes means for comparing said indicated rate signals to preset respective thresholds and means for limiting said combined rate signal if only one of said indicated rate exceeds the corresponding threshold.

14. The pacemaker of claim 8 wherein said metabolic rate responsive means includes monitoring means for monitoring a pulmonary function of said patient.

15. The pacemaker of claim 14 wherein said monitoring means includes impedance means for measuring a minute volume variation.

16. The pacemaker of claim 8 wherein said activity rate responsive means includes acceleration monitoring means for monitoring a physical acceleration signal responsive to physical activity of said patient.

17. The pacemaker of claim 16 wherein said acceleration monitoring means includes an acceleration detector monitoring said acceleration signal, first comparator means for detecting when said acceleration signal exceeds a preselected value and counter means coupled to said comparator sensors for counting a number indicative of said activity.

18. The pacemaker of claim 17 wherein said acceleration monitoring means further includes filter means for filtering said number.

19. The pacemaker of claim 18 wherein said filter means generates a time varying acceleration indicative profile having an initial segment indicative of physical activity onset, a median portion indicative of ongoing physical activity and a terminal portion indicative of an end of said physical activity.

20. The pacemaker of claim 19 wherein said monitoring means further includes scaler means for scaling said profile to a range corresponding to a range of said metabolic indicated rate.

21. A pacemaker comprising:

metabolic rate means for generating a metabolic indicated rate (MIR) signal dependent on a metabolic function of a patient;

activity rate means for generating an activity indicated rate (AIR) signal dependent on a physical parameter indicative of a level of physical activity of said patient;

combining means for combining said metabolic and activity indicated rate signals into a dual indicated rate (DIR) signal in accordance with a plurality of preselected rules, said rules being selected to augment said metabolic indicated rate signal by said activity indicated rate signal during a transition of said physical parameter; and pacer means for generating pacing signals responsive to said dual indicated rate signal.

22. The pacemaker of claim 21 wherein combining means includes means for monitoring said MIR and AIR signals, said monitoring means limiting said DIR signal to a preselected level if (a) the MIR is near a maximum level and (b) if AIR is near a minimum level.

23. The pacemaker of claim 22 wherein said preselected level is a predetermined amount above said minimum level.

24. The pacemaker of claim 22 wherein combining means cannot boost said MIR signal with said AIR signal above a threshold.

25. The pacemaker of claim 24 wherein said DIR signal has a predetermined maximum and a predetermined minimum and wherein said threshold is the average of said maximum and said minimum.

26. The pacemaker of claim 24 wherein during said transition, said DIR signal follows said AIR signal.

27. The pacemaker of claim 26 wherein except at said transition, said DIR signal follows said MIR signal.

28. The pacemaker of claim 21 wherein said combining means comprises a plurality of fuzzy logic circuits for implementing said rules.

29. The pacemaker of claim 28 wherein said fuzzy logic circuits include membership function blocks.

* * * * *